United States Patent [19]

Watanabe et al.

[11] 4,376,209

[45] Mar. 8, 1983

[54] PROCESS FOR PRODUCTION OF ETHYLENE OXIDE

[75] Inventors: Fumio Watanabe, Kawasaki; Masashi Mitsuhata; Toshihiko Kumazawa, both of Yokohama, all of Japan

[73] Assignee: Nippon Shokubai Kagaku Kogyo Co., Ltd., Japan

[21] Appl. No.: 188,464

[22] Filed: Sep. 18, 1980

Related U.S. Application Data

[63] Continuation of Ser. No. 60,744, Jul. 25, 1979, abandoned.

[30] Foreign Application Priority Data

Jul. 26, 1978 [JP] Japan ............................ 53-90462

[51] Int. Cl.$^3$ .................................... C07D 301/10
[52] U.S. Cl. ........................................ 549/534
[58] Field of Search .................. 260/348.34; 549/534

[56] References Cited

U.S. PATENT DOCUMENTS

| 3,147,084 | 9/1964 | Franzen et al. | 260/604 R |
| 4,012,425 | 3/1977 | Nielsen et al. | 260/348.34 |
| 4,061,659 | 12/1977 | Nielsen et al. | 260/348.34 |
| 4,169,099 | 9/1979 | Khoobiar | 260/348.34 |
| 4,267,073 | 5/1981 | Neilsen et al. | 260/348.34 |

FOREIGN PATENT DOCUMENTS 1449091  9/1976  United Kingdom .

OTHER PUBLICATIONS

C. J. Hilado et al., J. Fire & Flammability, vol. 6 (Jan. 1975), pp. 44–49.

*Primary Examiner*—Norma S. Milestone
*Attorney, Agent, or Firm*—Omri M. Behr

[57] ABSTRACT

A process for the production of ethylene oxide by the vapor-phase catalytic oxidation of ethylene with molecular oxygen, which process comprises passing a mixed gas containing ethylene and molecular oxygen through a catalyst bed filled with a silver catalyst and subsequently passing the resultant reaction product gas through a cooling zone filled with a particulate material containing a substance capable of inhibiting the isomerization of ethylene oxide to acetaldehyde carrying at least one metal selected from the group consisting of sodium, potassium, rubidium, cesium, calcium, strontium, barium and thallium or a compound of said metal to be carried on an inert refractory particulate material.

11 Claims, No Drawings

PROCESS FOR PRODUCTION OF ETHYLENE OXIDE

This application is a continuation of application Ser. No. 060,744, filed July 25, 1979, now abandoned.

BACKGROUND OF THE INVENTION

1. Field of the Invention

This invention relates to a process for the production of ethylene oxide. More particularly, it relates to a process for the production of ethylene oxide of high purity in high yields by introducing reactant ethylene and a molecular oxygen containing gas into a catalyst bed filled with a silver catalyst and subsequently causing the reaction product gas containing the formed ethylene oxide and issuing from the catalyst bed to be passed through a cooling zone filled with a carrier containing a metal capable of inhibiting isomerization of ethylene oxide to acetaldehyde.

2. Description of the Prior Arts

In processes for the production of ethylene oxide by the vapor-phase catalytic oxidation of ethylene with molecular oxygen, a major concern of those engaging in the art resides in the problem as to how ethylene oxide is produced in high yields with high productivity and at high purity. In search of a solution to this problem, numerous studies have been carried out and various efforts made to date. They have been preponderantly directed to improvement of catalysts and improvement of reaction conditions. Of the various subjects of studies, the improvement of catalysts has constituted itself the most important problem. Numerous efforts have been focussed on the improvement of catalysts' qualities.

As is widely known, in the production of ethylene oxide by the vapor-phase catalytic oxidation of ethylene with molecular oxygen in the presence of silver catalyst, the reaction proceeds as represented by formula I shown below.

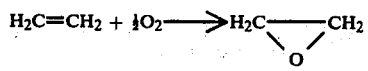  (I)

This reaction, however, is susceptible of simultaneously entailing side reaction, which are represented by a so-called perfect oxidizing reaction of a mechanism as expressed below by formula II.

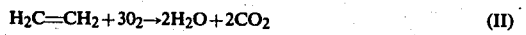  (II)

The extent to which the reaction of formula II is suffered to occur depends on the quality of the catalyst in use. This explains why the improvement of catalysts has constituted one major task for the researches.

In addition to the reactions of formula I and formula II indicated above, there is another reaction which affects the yield of ethylene oxide. It is isomerization of ethylene oxide to acetaldehyde which proceeds as represented by formula III below.

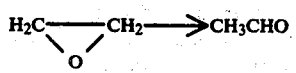  (III)

No matter how high the selectivity of the conversion of ethylene to ethylene oxide may be, the yield of ethylene oxide is lowered when the ratio of isomerization of the formed ethylene oxide to acetaldehyde is increased. An addition to the acetaldehyde content of the product stream results in a proportional increase in the expense incurred in the refining of the product stream for the isolation of ethylene oxide at high purity. In this respect, therefore, minimization of the isomerization of ethylene oxide to acetaldehyde poses itself as one of the important tasks in the way of the production of ethylene oxide.

Generally in processes for partial oxidation of hydrocarbons, it is known to preclude possible occurrence of side reactions by passing the reaction product gas through a cooling zone filled with packing (U.S. Pat. No. 3,147,084 to E. P. Franzen et al). It is also known to apply such a method to the processes for the production of ethylene oxide by the vapor-phase catalytic oxidation of ethylene with molecular oxygen (British Pat. No. 1,449,091 to Snamprogetti and U.S. Pat. No. 4,061,659 to Nielsen et al). The British patent, for example, discloses a method resorting to passage of the reaction product from a reaction zone through a cooling zone being contiguous or not contiguous to a reaction zone and containing or not containing bodies of inert materials. The U.S. patent to Nielsen et al teaches a method resorting to passage of the reaction product through a cooling zone filled with an inert refractory particulate material having a surface area of 0.1 m²/g or less. These methods, however, are not sufficiently effective in providing satisfactory repression of the isomerization of ethylene oxide to acetaldehyde.

It has been ascertained by our studies that the isomerization of ethylene oxide to acetaldehyde has bearings upon the magnitude of the temperature of the reaction product gas containing the formed ethylene oxide, the residence time of the gas at elevated temperatures and the surface area in which the gas is exposed to contact with the articles of elevated temperatures. Repression of the isomerization is advantageously accomplished, therefore, by a method capable of lowering the temperature of the ethylene oxide containing gas, a method of shortening the residence time at elevated temperatures or a method of decreasing the surface area of contact with the articles of elevated temperatures.

In ordinary conventional processes for the production of ethylene oxide, the hot reaction product containing the formed ethylene oxide and issuing from the reactor is led to an ethylene oxide absorption tower, wherein it is recovered by absorption in water kept at a temperature below 35° C. Generally, prior to delivery to the absorption tower, the gas is cooled down to a proximity of room temperature by means of a varying heat exchanger. In the interval between the outlet of the catalyst bed and the inlet of the heat exchanger, however, the reaction product gas containing the formed ethylene oxide is left to cool spontaneously or subjected partially to forced cooling by means of a coolant and, consequently, is suffered to remain at a temperatuure above 200° C. This retention of the gas at the high temperature forms a main cause for the isomerization of ethylene oxide to acetaldehyde. It would appear to be effective, therefore, to cool the reaction product gas suddenly to a temperature below 200° C. in this interval. On account of the expense required for the particular step of sudden cooling and in the light of the economics of commercial operation of the whole process, it is not necessarily advantageous to relay solely on the step of sudden cooling for the repression of isomerization. In fact, it is difficult to obtain thorough repression of the isomerization merely by this step of sudden cooling.

As more advantageous means of effectively repressing the isomerization of ethylene oxide to acetaldehyder, it may be necessary to devise a method for shortening the residence time of the gas at elevated temperatures and providing efficient cooling of the gas. For this purpose, there is apparent necessity of using a packing carried in a cooling zone which is formed in the interval between the catalyst bed and the heat exchanger where the gas has a temperature of not lower than 150° C. As the packing, it is desirable from the physical and economic points of view to use an inert refractory particulate material of the kind used for the production of a silver catalyst. Of course, other kinds of packings may be used for this purpose on condition that due consideration be paid to factors such as mechanical strength, weight, pressure loss and economics.

One important consideration required at this point, however, is that the act of filling the empty space with a packing results in an addition to the area of contact of the reaction product gas, which in turn accelerates the isomerization of ethylene oxide in utter contradiction to what is aimed at by the packing. Most packings are such that at temperatures required for the formation of ethylene oxide, they accelerate the isomerization of ethylene oxide to acetaldehyde in the surface of contact thereof with the reaction product gas containing the formed ethylene oxide. The inert refractory particulate material previously described as forming a substance desirable for the production of silver catalyst is no exception. On the contrary, the inert refractory particulate material, when given a large specific surface area, may well be regarded as contributing more to accelerating the isomerization than any other material.

An object of the present invention, therefore, is to provide a process for the production of ethylene oxide of high purity in high yields by repressing the isomerization to acetaldehyde of the ethylene oxide formed by the vapor-phase catalytic oxidation of ethylene with molecular oxygen.

Another object of the invention is to provide a process for the production of ethylene oxide in high yields by increasing the oxygen concentration in the influent mixed gas used for the production of ethylene oxide.

SUMMARY OF THE INVENTION

These objects are accomplished by a process for the production of ethylene oxide by the vapor-phase catalytic oxidation of ethylene with molecular oxygen, which process comprises passing a mixed gas containing ethylene and molecular oxygen through a catalyst bed filled with a silver catalyst and subsequently passing the resultant reaction product gas through a cooling zone filled with a particular material containing a substance capable of inhibiting the isomerization of ethylene oxide to acetaldehyde carrying at least one metal selected from the group consisting of sodium, potassium, rubidium, cesium, calcium, strontium, barium and thallium or a compound of said metal to be carried on an inert refractory particulate material.

It has been found that the use of the aforementioned particulate material containing the isomerization inhibiting metal, as contemplated by the present invention, brings about the advantage of eliminating the drawbacks arising from the increase in the specific surface area of a packing, permitting full utilization of the decrease in the retention time and the increase in the thermal conduction efficiency due to the packing, and ensuring repression of the isomerization of ethylene oxide to acetaldehyde.

The isomerization of ethylene oxide to acetaldehyde occurs on the surface of an article at an elevated temperature. No entire surface of the article has one and the same temperature and exhibit uniform activity. Instead, the surface exhibits greater activity in some portions and lesser activity in other portions, namely portions of the nature of active points are present on the surface. In the case of an article possessing a large specific surface area, consequently, there is a possibility that such portions will be present in a larger number. Besides, a large specific surface area naturally implies a smaller pore diameter and likely affects the temperature distribution, gas diffusion and residence time. This may explain why such an article suffers more from the isomerization. When the article being used has a very small specific surface area, the isomerization suffered to occur will be proportionally small. No total elimination of the isomerization, however, is possible. In practising a technique of decreasing the formation of acetaldehyde by use of a packing, a special operation required for the preparation of a packing possessing a specific surface area small enough for the purpose will prove both uneconomical and complicate. It is, therefore, desirable to repress the isomerization of ethylene oxide to acetaldehyde by means of a packing equalling an inert refractory particulate material used in the preparation of a silver catalyst for a catalyst bed. The inert refractory carrier for the silver catalyst generally used in the form of a catalyst bed often has a specific surface area exceeding 0.1 m$^2$/g, though it occasionally has a smaller specific surface area. Thus, this carrier proves detrimental in that it accelerates the isomerization of ethylene oxide to acetaldehyde. According to the present invention, however, the inert refractory particulate material can be effectively carried as the result of a simple treatment without reference to the specific surface area of the material and can be operated advantageously to repress the isomerization of ethylene oxide to acetaldehyde.

PREFERRED EMBODIMENT OF THE INVENTION

According to this invention, ethylene oxide having a low acetaldehyde content can be produced by the steps of passing a mixed gas containing ethylene and molecular oxygen through a catalyst bed filled with a silver catalyst and subsequently causing the reaction product gas issuing from the catalyst bed to be passed through a cooling zone formed over a part or the whole of the downstream zone extending from the outlet of the catalyst bed to the terminal point at which the passing reaction product gas has a temperature of not lower than 150° C., with the cooling zone being filled with an inert refractory particulate material containing a metal capable of inhibiting the isomerization of ethylene oxide, i.e., a material prepared by depositing on an inert refractory particulate substance 0.00001 to 1.0 gram equivalent, based on 1 kg of said particulate substance, of at least one metal selected from the group consisting of sodium, potassium, rubidium, cesium, calcium, strontium, barium and thallium or a compound of said metal.

The inert refractory particulate material to be used in the present invention may be in any of the various forms such as, for example, spheres, semispheres, pellets, rings and irregularly shaped particles insofar as it is made of an inert refractory substance. It is desired to be made of alumina, silica-alumina, zirconia, magnesia, silicon carbide, etc. generally used as the carrier for a silver catalyst, preferably of alpha-alumina and zirconia. The shape, size, specific surface area, apparent porosity, etc. of the particulate material can be suitably selected in due consideration of the pressure loss and the mechanical strength when the cooling zone is filled with this material. The average particle diameter of the particulate material is generally from 1/16 to ½ inch, preferably from 3/16 to ¼ inch. The particles are desired to be in the shape of spheres or rings. The specific surface area is not more than 20 $m^2/g$, desirably falling in the range of from 0.1 to 10 $m^2/g$, preferably exceeding 0.1 $m^2/g$ and not exceeding 5 $m^2/g$. The apparent porosity is desired to be at least 20% by volume, preferably falling in the range of from 30 to 70% by volume.

The substances which inhibit the isomerization and are usable as carried in the inert refractory particulate material of this invention are sodium, potassium, rubidium, cesium, calcium, strontium, barium and thallium. Of these substances, sodium, potassium, rubidium, cesium and thallium are more desirable than the others. Cesium and thallium are preferred to all the other. These substances are usable in the form of various compounds such as inorganic acid salts including oxides, hydroxides, nitrates, sulfates, carbonates and hydrogencarbonates and organic acid salts including acetates, formates, lactates and oxalates. It is particularly desirable to use such substances in the form of compounds soluble in water. The required deposition of a substance selected from the aforementioned group on the inert refractory particulate material is accomplished most desirably by impregnating the particulate material in an aqueous solution of the substance, concentrating the solution containing the impregnated particulate material, and drying the concentrated solution in the atmosphere of a suitable gas such as air, carbon dioxide gas or nitrogen gas at a temperature in the range of from 50° to 300° C., preferably from 90° to 200° C., for a period of from one to 24 hours. Otherwise, the deposition may be effected by causing the selected substance to be mixed with the inert refractory material before the material is molded into its particulate form. The amount in which the metal or the compound thereof is added to the particulate material is generally from 0.00001 to 1.0 gram equivalent, preferably from 0.0001 to 0.1 gram equivalent, based on 1 kg of the particulate material. The metal or the compound thereof used in excess of the upper limit of the range specified above produces no additional effect. The isomerization-inhibiting substance thus deposited on the particulate material is in the form of a metal or metal compound.

As a matter of course, the cooling zone filled with the particulate material containing the isomerization-inhibiting substance is required only to encompass a portion at high temperatures, namely the portion forming the whole or a part of the downstream zone generally extending from the outlet of the catalyst bed to the heat exchanger as described above, wherein the passing gas has temperatures above 150° C. Although the cooling can be effected either spontaneously or by a commonly practiced forced-cooling technique, it is desired to be effected externally by means of water or a well-known coolant. Generally in the production of ethylene oxide by the vapor-phase catalytic oxidation of ethylene with molecular oxygen, the oxidation reaction is carried out at temperatures in the range of from 150° to 400° C. As a natural consequence, the reaction production gas rises to a higher temperature and consequently induces isomerization of the formed ethylene oxide to acetaldehyde. Thus, the cooling zone filled with the aforementioned particulate material is desired to be formed in the zone wherein the passing reaction product gas has temperatures above 150° C., preferably above 200° C.

Incorporation of the cooling zone of this invention which is filled with the particulate material containing the substance capable of inhibiting the isomerization of ethylene oxide brings about a major effect besides the effect of repressing the isomerization of ethylene oxide to acetaldehyde: To be specific, the cooling zone has an effect of permitting the concentration of oxygen in the reactant mixed gas to be increased in the reaction zone and consequently heightening the selectivity of the reaction to ethylene oxide. Generally, the concentration of oxygen in the reaction mixed gas is kept below the explosion limit for the safety of operation as is naturally expected. From the standpoint of selectivity, however, the concentration of oxygen is desired to be as high as permissible. A number of studies have been under way in search of methods for heightening the concentration of oxygen without jeopardizing the operational safety, and some of them have brought about successful results. An increase in the concentration of oxygen in the reactant mixed gas necessitates selection of conditions under which the concentration of oxygen can be increased independently of the explosion limit of the mixed gas or adoption of a measure capable of preventing the mixed gas from explosion or combustion even when the composition of the mixed gas falls in the range of explosion.

It is widely known that the range of explosion is varied by the temperature, pressure, thermal capacity, etc. of the gas involved. The heighest concentration of oxygen tolerated outside the range of explosion increases in proportion as the temperature and pressure of the gas decrease and the thermal capacity of the gas increases. Our experiment has demonstrated that the range of explosion is also affected by the stationary and fluid states of the gas involved. Specifically, it has been ascertained that the range of explosion is smaller when the gas is flowing than when it is at rest and that, when the gas is flowing, the range of explosion decreases with the increasing flow rate of the gas. It has been found further that the range of explosion is affected by the ratio of the volume of the space occupied by the gas to the surface area of the enclosure encompassing the space, namely that the highest permissible concentration of oxygen increases with the decreasing volume/surface area ratio.

All these observations indicate that the concentration of oxygen can be increased more safely by heightening the flow rate of the gas and decreasing the volume/surface area ratio and that incorporation of a packing at a portion wherein the explosive gas is in motion fulfills the purpose just right. This knowledge has added all the more to the practical utility of this invention.

The interposition between the catalyst bed and the heat exchanger of the cooling zone filled with the particulate material containing the substance capable of inhibiting the isomerization of ethylene oxide not only serves to diminish the possibility of explosion of the explosive gas at elevated temperatures, namely the reaction product gas containing ethylene, ethylene oxide and oxygen and issuing from the catalyst bed, but also permits an increase in yields owing to an increased concentration of oxygen in the reactant mixed gas and consequently in the reaction product gas. The incorporation of the particulate material containing the substance capable of inhibiting the isomerization of ethylene oxide permits the concentration of oxygen in the reactant mixed gas to be increased by 2 to 3% from the highest level permissible in the equipment involving identical operation conditions and not incorporating the cooling zone.

In the process of this invention, the cooling zone filled with the particulate material containing the the substance capable of inhibiting the isomerization of ethylene oxide occupies the whole or a part of the downstream zone extending between the outlet of the catalyst bed and the heat exchanger as described above, or more desirably the whole or a part of the zone between the outlet of the catalyst bed and the outlet of the reactor containing the catalyst bed, specifically between the upper part of the catalyst bed and the gas outlet of the channel section of the reactor.

The process of this invention can be applied to any of the processes and reaction conditions heretofore known to the art. The processes generally adopted for the production of ethylene oxide by the vapor-phase catalytic oxidation of ethylene with molecular oxygen are broadly divided by the source of oxygen into two groups, the processes resorting to air oxidation and those of oxygen oxidation. This invention can be applied effectively to both groups of the conventional processes. The invention is more effectively applicable to the oxygen oxidation group of processes wherein the volume of the per-pass reactant mixed gas can be increased and consequently the ethylene oxide concentration in the reaction product gas can be increased.

The operating conditions are widely variable. The reactant mixed gas is generally composed of ethylene, oxygen, carbon dioxide, nitrogen, argon, methane, ethane, and a reaction inhibitor. Although the economy of operation apparently increases with the increasing concentration of ethylene in the reactant mixed gas, the concentration of ethylene should be controlled below 40% by volume in due consideration of the possible absorption loss of ethylene within the absorption tower. The carbon dioxide gas functions to inhibit the reaction, so that the concentration of this gas should not be very high but should be kept below 10% by volume. When the reactant mixed gas contains methane or ethane, since methane plays the role of shifting the range of explosion toward the safety side or decreasing the range of explosion, it is advantageous for the reactant mixed gas to contain methane in a fairly high concentration as its diluent. In the case of ethane, since it lacks the effect just mentioned and functions to degrade the selectivity of reaction to ethylene oxide, it is desired to be controlled to the lowest possible concentration. A halide as a reaction inhibitor evidently serves to improve the selectivity of reaction to ethylene oxide. Thus, addition of the halide in a proper amount proves advantageous.

The reaction pressure is in the range of from 0 to 40 kg/cm$^2$G, preferably from 10 to 30 kg/cm$^2$G. The reaction temperature is in the range of from 150° to 400° C., preferably from 180° to 280° C. The space velocity is in the range of from 1,000 to 10,000 hr$^{-1}$ and preferably from 2,000 to 8,000 hr$^{-1}$.

The catalyst which is used to fill the catalyst bed may be any of the conventionally known silver catalysts. It is, however, preferable to use a silver catalyst prepared by having finely divided metallic silver deposited on an inert refractory carrier which possesses a specific surface area of not more than 20 m$^2$/g. desirably ranging from 0.01 to 10 m$^2$/g. preferably exceeding 0.1 m$^2$/g and not exceeding 5 m$^2$/g, and an apparent porosity of not less than 20% by volume, preferably ranging from 20 to 70% by volume. Examples of the materials which can be used as the inert refractory carrier include alpha-alumina, silica-alumina, silicon carbide, zirconia and magnesia. It is particularly desirable to use an inert refractory carrier formed preponderantly of alpha-alumina. The carrier can be used in any of the shapes including spheres, hemispheres, rings, pellets and tablets, for example. Spheres and rings are preferred to the other shapes. The carrier particles are desired to possess a particle diameter in the range of from 1/16 to ½ inch, preferably from 3/16 to ⅓ inch. The amount of silver thus deposited in the catalyst may be in the range of from 1 to 20% by weight, and economically in the range of from 2 to 8% by weight.

The present invention will be described more specifically by reference to working examples and controls cited herein below. The examples are not meant as limitations to this invention but admit of modifications thereto without departing from the spirit of the invention.

EXAMPLE 1

In an aqueous solution containing 0.1% by weight of sodium nitrate, 1 liter of an alpha-alumina carrier having a specific surface area of 0.3 m$^2$/g, an apparent porosity of 55 to 60% by volume and a particle diameter of 4 to 6 mm was immersed. The impregnated carrier was drained of excess aqueous solution and then dried in the atmosphere of air at 90° to 150° C. for five hours. The amount of sodium consequently deposited on the carrier was as shown in Table 1.

The carrier thus obtained was placed to fill a stainless steel reactor tube 18.5 mm in inside diameter and 5 m in length. With the outside of the reactor tube maintained at 250° C. by means of a heat transfer medium "Dowtherm A," a mixed gas consisting of 1.7% by volume of ethylene oxide, 13% by volume of ethylene, 5% by volume of oxygen, 7% by volume of carbon dioxide and the balance to make up 100% by volume of nitrogen was introduced into the reactor tube under a pressure of 25 kg/cm$^2$ at a flow rate of 90 liters/min. The conversion of the ethylene oxide in the mixed gas to acetaldehyde was a shown in Table 1.

EXAMPLES 2-8

The procedure of EXAMPLE 1 was repeated, except that the kind and amount of the substance added to be deposited on the inert refractory carrier was varied as indicated in Table 1. The results were as shown in Table 1.

EXAMPLES 9-11

The procedure of EXAMPLE 1 was repeated, except that the carrier was varied as indicated in Table 1. The results were as shown in Table 1.

EXAMPLE 12

The procedure of EXAMPLE 1 was repeated, except that the layer filled with the carrier was kept at 200° C. The results were as shown in Table 1.

CONTROLS 1-4

The procedure of EXAMPLE 1 was repeated, except that varying inert refractory carriers indicated in Table 1 were used and no additive was used in the carriers. The results were as shown in Table 1.

CONTROL 5

The procedure of EXAMPLE 1 was repeated, except that no additive was used in the carrier and the layer filled with the carrier was kept at 130° C. The results were as shown in Table 1.

TABLE 1

| | Inert refractory particulate material | | | | Substance added | | | |
|---|---|---|---|---|---|---|---|---|
| | | | | | | Amount added | | |
| | Main ingredient | Porosity (% by volume) | Particle diameter (mm) | Specific surface area ($m^2/g$) | Compound | (g. equivalent based on 1 kg of particulate material) | Temperature of packed bed (°C.) | Conversion of ethylene oxide (%) |
| EXAMPLE | | | | | | | | |
| 1 | alpha-alumina | 55-60 | 5 | 0.3 | $NaNO_3$ | $4.6 \times 10^{-3}$ | 250 | 0.2 |
| 2 | alpha-alumina | 55-60 | 5 | 0.3 | $KNO_3$ | $2.8 \times 10^{-3}$ | 250 | 0.2 |
| 3 | alpha-alumina | 55-60 | 5 | 0.3 | $PbNO_3$ | $2.8 \times 10^{-3}$ | 250 | 0.2 |
| 4 | alpha-alumina | 55-60 | 5 | 0.3 | $CsNO_3$ | $1.9 \times 10^{-3}$ | 250 | 0.1 |
| 5 | alpha-alumina | 55-60 | 5 | 0.3 | $Ca(NO_3)_2$ | $9.2 \times 10^{-3}$ | 250 | 0.4 |
| 6 | alpha-alumina | 55-60 | 5 | 0.3 | $Sr(NO_3)_2$ | $4.6 \times 10^{-3}$ | 250 | 0.4 |
| 7 | alpha-alumina | 55-60 | 5 | 0.3 | $Ba(NO_3)_2$ | $9.2 \times 10^{-3}$ | 250 | 0.2 |
| 8 | alpha-alumina | 55-60 | 5 | 0.3 | $Tl(NO_3)_2$ | $1.1 \times 10^{-3}$ | 250 | 0.1 |
| 9 | alpha-alumina | 60-65 | 5 | 1.63 | $CsNO_3$ | $10.1 \times 10^{-3}$ | 250 | 0.3 |
| 10 | alpha-alumina | 62-68 | 5 | 8.63 | $CsNO_3$ | $53.3 \times 10^{-3}$ | 250 | 0.4 |
| 11 | zirconia | 40-45 | 3 | 0.06 | $CsNO_3$ | $1.0 \times 10^{-3}$ | 250 | 0.2 |
| 12 | alpha-alumina | 55-60 | 5 | 0.3 | $CsNO_3$ | $1.9 \times 10^{-3}$ | 200 | 0.0 |
| CONTROL | | | | | | | | |
| 1 | zirconia | 40-45 | 3 | 0.06 | — | — | 250 | 1.1 |
| 2 | alpha-alumina | 55-60 | 5 | 0.3 | — | — | 250 | 4.3 |
| 3 | alpha-alumina | 60-65 | 5 | 1.63 | — | — | 250 | 13.1 |
| 4 | alpha-alumina | 62-68 | 5 | 8.63 | — | — | 250 | 64.6 |
| 5 | alpha-alumina | 55-60 | 5 | 0.3 | — | — | 130 | 0.0 |

What is claimed is:

1. A process for the production of ethylene oxide by the vapor-phase catalytic oxidation of ethylene with molecular oxygen, which process comprises passing a mixed gas containing ethylene and molecular oxygen through a catalyst bed filled with a silver catalyst and subsequently passing the resultant reaction product gas through a cooling zone filled with a particulate material having a specific surface area exceeding 0.1 $m^2/g$ but not exceeding 5 $m^2/g$, containing a substance capable of inhibiting the isomerization of ethylene oxide to acetaldehyde containing at least one metal selected from the group consisting of calcium, strontium and barium or a compound of said metal to be carried on an inert refractory particulate material.

2. A process according to claim 1, wherein the substance capable of inhibiting the isomerization of ethylene oxide to acetaldehyde is carried in an amount of from 0.00001 to 1.0 gram equivalent based on 1 kg of the inert refractory particulate material.

3. A process according to claim 1, wherein the substance capable of inhibiting the isomerization of ethylene oxide to acetaldehyde is carried in an amount of from 0.0001 to 0.1 gram equivalent based on 1 kg of the inert refractory particulate material.

4. A process according to claim 1, wherein the cooling zone filled with the particulate material containing the substance capable of inhibiting the isomerization of ethylene oxide to acetaldehyde is formed in a portion extending from the outlet of the catalyst bed to the terminal point at which the passing reaction product gas has a temperature of not lower than 150° C.

5. A process according to claim 2, wherein the cooling zone filled with the particulate material containing the substance capable to inhibiting the isomerization of ethylene oxide to acetaldehyde is formed in a portion extending from the outlet of the catalyst bed to the terminal point at which the passing reaction product gas has a temperature of not lower than 200° C.

6. A process according to claim 1, wherein the inert refractory particulate material is formed preponderantly of at least one member selected from the group consisting of alpha-alumina, silica-alumina, zirconia, magnesia and silicon carbide.

7. A process according to claim 6, wherein the main ingredient of the inert refractory particulate material is one member selected from the group consisting of alpha-alumina and zirconia.

8. A process according to claim 7, wherein the main ingredient of the inert refractory particulate material is alpha-alumina.

9. A process according to claim 6, wherein the inert refractory particulate material has the shape of spheres or rings.

10. A process according to claim 6, wherein the inert refractory particulate material has an average particle diameter of from 3/16 to ½ inch.

11. A process according to claim 1, wherein the inert refractory particulate material has an apparent porosity of not less than 20% by volume.

* * * * *